(12) United States Patent
Gabbay

(10) Patent No.: US 7,247,167 B2
(45) Date of Patent: Jul. 24, 2007

(54) LOW PROFILE HEART VALVE PROSTHESIS

(76) Inventor: Shlomo Gabbay, #1 Randall Dr., Short Hills, NJ (US) 07078

( * ) Notice: Subject to any disclaimer, the term of this patent is extended or adjusted under 35 U.S.C. 154(b) by 415 days.

(21) Appl. No.: 10/782,702

(22) Filed: Feb. 19, 2004

(65) Prior Publication Data

US 2005/0187618 A1   Aug. 25, 2005

(51) Int. Cl.
*A61F 2/24* (2006.01)

(52) U.S. Cl. ............ 623/2.14; 623/2.18; 623/2.38

(58) Field of Classification Search ...... 623/2.14–2.19, 623/2.38, 904, 2.4, 2.12, 2.13, 2.39; 600/37
See application file for complete search history.

(56) References Cited

U.S. PATENT DOCUMENTS

| | | | |
|---|---|---|---|
| 3,739,402 A | 6/1973 | Cooley et al. | |
| 3,744,060 A | 7/1973 | Bellhouse et al. | |
| 3,983,581 A * | 10/1976 | Angell et al. | 623/2.15 |
| 4,084,268 A * | 4/1978 | Ionescu et al. | 623/2.15 |
| 4,106,129 A * | 8/1978 | Carpentier et al. | 623/2.18 |
| 4,247,292 A | 1/1981 | Angell et al. | |
| 4,388,735 A * | 6/1983 | Ionescu et al. | 623/2.19 |
| 4,470,157 A * | 9/1984 | Love | 623/2.15 |
| 4,477,930 A | 10/1984 | Totten et al. | |
| 4,626,255 A * | 12/1986 | Reichart et al. | 623/2.13 |
| 4,629,459 A * | 12/1986 | Ionescu et al. | 623/2.15 |
| 4,759,758 A | 7/1988 | Gabbay | |
| 5,032,128 A * | 7/1991 | Alonso | 623/2.41 |
| 5,156,621 A | 10/1992 | Navia et al. | |
| 5,258,023 A * | 11/1993 | Reger | 623/2.18 |
| 5,336,258 A | 8/1994 | Quintero et al. | |
| 5,549,665 A | 8/1996 | Vesely et al. | |
| 5,713,950 A | 2/1998 | Cox | |
| 5,855,602 A | 1/1999 | Angell | |
| 5,861,028 A | 1/1999 | Angell | |
| 5,935,163 A * | 8/1999 | Gabbay | 623/2.14 |
| 6,102,944 A | 8/2000 | Huynh et al. | |
| 6,264,691 B1 * | 7/2001 | Gabbay | 623/2.14 |
| 6,610,088 B1 | 8/2003 | Gabbay | |

* cited by examiner

*Primary Examiner*—Alvin J. Stewart
(74) *Attorney, Agent, or Firm*—Tarolli, Sundheim, Covell & Tummino LLP

(57) ABSTRACT

A heart valve prosthesis includes a valve member having an inflow end, an outflow end, and a generally cylindrical sidewall portion extending between the inflow end and the outflow end. The valve member includes at least one leaflet moveable relative to the sidewall portion to provide for substantially unidirectional flow of fluid through the valve member. A support of a substantially flexible material positioned is around the sidewall portion. A strip of pliant material is provided around valve member intermediate the inflow end and the outflow end of the valve member in a generally overlying relationship with the support. A covering is provided over a radially outer exposed surface of at least the strip.

12 Claims, 2 Drawing Sheets

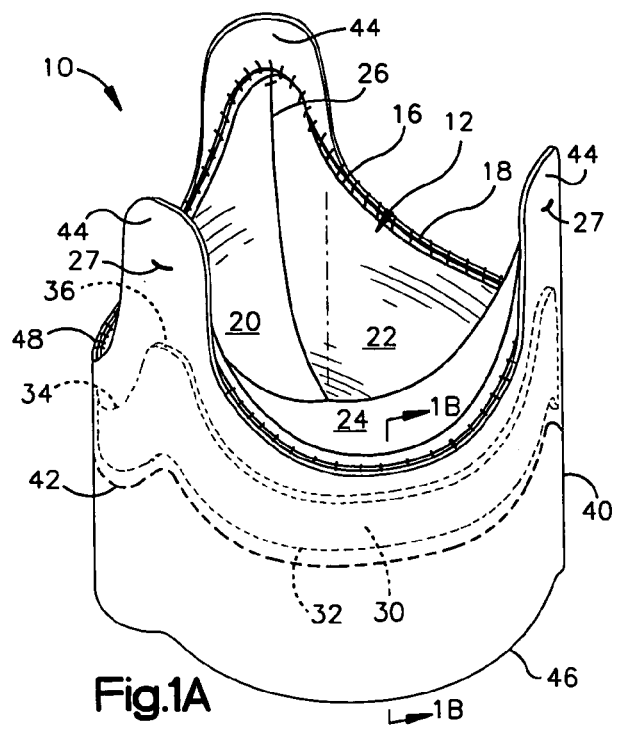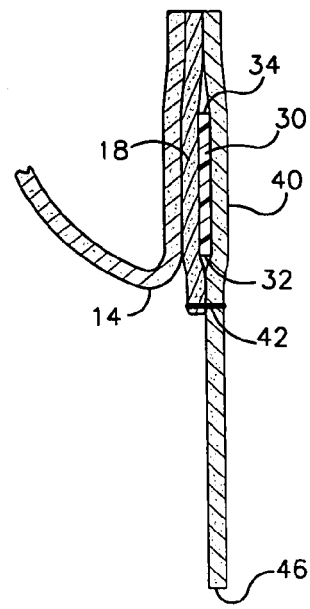
Fig.1A  Fig.1B
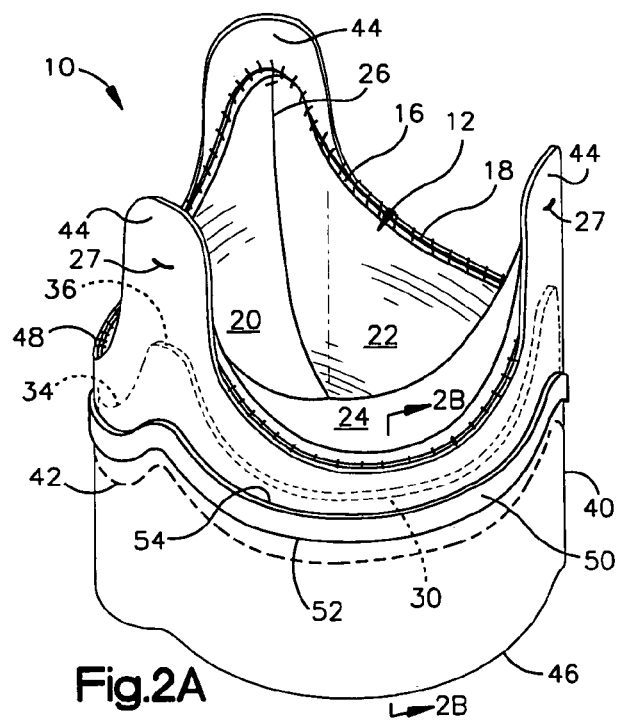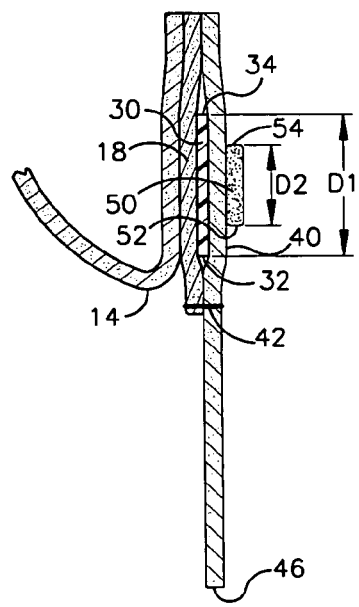
Fig.2A  Fig.2B

LOW PROFILE HEART VALVE PROSTHESIS

TECHNICAL FIELD

The present invention relates to a bio-prosthesis, and more particularly to a heart valve prosthesis having a low profile.

BACKGROUND OF THE INVENTION

Numerous types of heart valve prostheses have been developed for replacing defective heart valves in human patients. One common type of heart valve prosthesis includes a natural tissue heart valve mounted within a stent. The stent generally provides strength and rigidity to the heart valve. Typically, the stent is covered with a textile material, such as Dacron™, which provides a substrate to which the heart valve may be secured. While the stent provides desired rigidity and strength, which inhibits the inward deflection of the stent posts, it also decreases the hemodynamics of the valve. This is because the stent substantially increases the sidewall thickness of the prosthesis, which reduces the size of the flow orifice for a prosthesis having a given outer diameter. The exposed textile covering also tends to abrade cusps of the valve.

In order to overcome the disadvantages associated with the stented heart valve prosthesis, there has been an increasing tendency to form natural tissue heart valve prostheses with no stent. These are called stentless valves. Stentless valves exhibit improved hemodynamics and are less resistant to blood flow. In addition, stentless valves, as compared to stented valves, are more resistant to structural failure because the rigidity of a stent can cause damage to the moving cusps. The improved hemodynamic characteristics of stentless valves can also cause beneficial remodeling of the heart muscle. For example, it has been determined that several months after implantation of a stentless valve in the aortic position, there is a noticeable improvement in the size of a left ventricle.

SUMMARY OF THE INVENTION

One aspect of the present invention provides a heart valve prosthesis that includes a valve member having an inflow end, an outflow end, and a generally cylindrical sidewall portion extending between the inflow end and the outflow end. The valve member includes at least one leaflet moveable relative to the sidewall portion to provide for substantially unidirectional flow of fluid through the valve member. A support of a substantially flexible material positioned is around the sidewall portion. A strip of pliant material is provided around valve member intermediate the inflow end and the outflow end of the valve member in a generally overlying relationship with the support. A covering is provided over a radially outer exposed surface of at least the strip.

Another aspect of the present invention provides a heart valve prosthesis includes a heart valve. The heart valve includes a generally cylindrical sidewall portion extending between an inflow end and an outflow end. At least one leaflet is located within the sidewall portion, the leaflet being moveable relative to the sidewall portion to provide for substantially unidirectional flow of blood through the heart valve. A support apparatus can be provided around the sidewall portion and positioned axially between the inflow end and the outflow end of the sidewall portion. A strip of pliant material is provided around the sidewall portion of the heart valve intermediate the inflow end and the outflow end of the sidewall portion and extending radially outwardly beyond a radially outer surface of the support. A pliable covering is applied over the strip and attached relative to the heart valve to inhibit axial movement of the strip relative to the heart valve.

BRIEF DESCRIPTION OF THE DRAWINGS

FIG. 1A is a perspective view of a heart valve prosthesis depicting a first fabrication stage according to an aspect of the present invention.

FIG. 1B is a partial cross-sectional view of the prosthesis of FIG. 1A

FIG. 2A is a perspective view of a heart valve prosthesis depicting a second fabrication stage according to an aspect of the present invention.

FIG. 2B is a partial cross-sectional view of the prosthesis of FIG. 2A

DETAILED DESCRIPTION

Figure 3A:
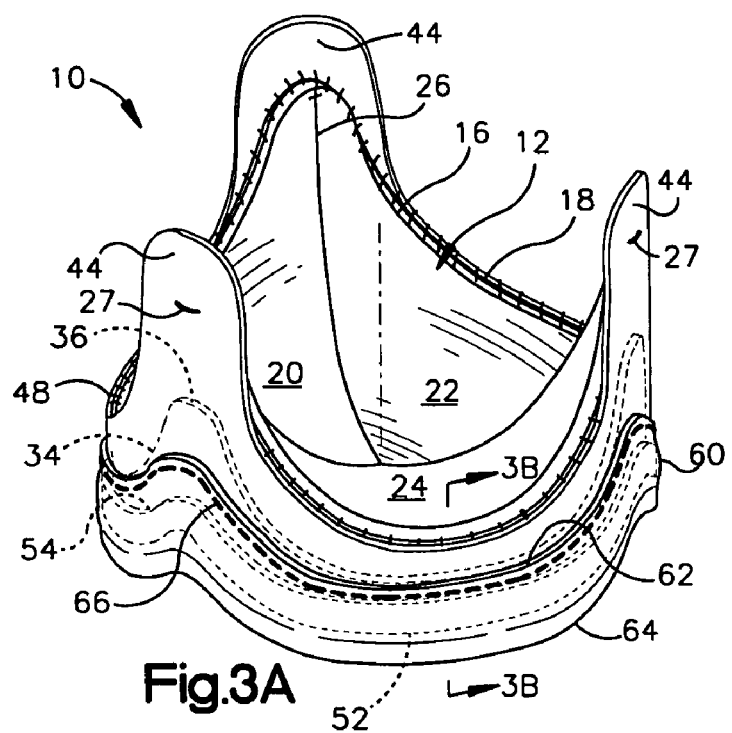
FIG. 3A is a perspective view of a heart valve prosthesis according to an aspect of the present invention.

FIGS. 1A through 3B illustrate an example of one embodiment of a heart valve prosthesis 10 being fabricated in accordance with an aspect with the present invention. Each of the FIGS. 1A, 2A, and 3A correspond to different possible stages of fabrication that can be utilized to provide the prosthesis 10. The resulting prosthesis 10 is shown in FIG. 3A.

Those skilled in the art will understand and appreciate that various other approaches can be employed to produce a heart valve prosthesis according to the present invention. Additionally, it will be understood and appreciated that the relative dimensions between the various parts of the prosthesis 10 depicted in the figures are shown for purposes of simplicity of illustration and that various other dimensions and configurations can be utilized.

Throughout the various figures, the prosthesis 10 includes a valve portion 12 arranged to provide for substantially unidirectional flow of blood through the valve portion 12. The valve portion 12 includes an inflow end 14 spaced apart from an outflow end 16 by a generally cylindrical sidewall portion 18. In the particular example of FIGS. 1A, 2A and 3A, the valve portion 12 is depicted as including a plurality of leaflets 20, 22 and 24 that extend from and are moveable relative to the associated sidewall portion 18.

For instance, the leaflets 20, 22 and 24 and sidewall portion can correspond to parts of a tri-leaflet valve that has been previously harvested and treated for implantation. Thus, the sidewall portion 18 can be formed of a corresponding valve wall of a biological heart valve (e.g., an aortic or pulmonic valve). For example, the valve portion 12 can be implemented as a homograft (e.g., excised from a human donor) or a xenograft (e.g., excised from an animal, such as a pig, cow or horse). As an alternative example, the valve portion 12 can be implemented as a manufactured valve that can include natural and/or synthetic materials. The valve portion 12 can include any number of one or more leaflets.

Commissures 26 are defined at the juncture of adjacent leaflets 20, 22 and 24. The outflow end 16 of the valve portion can have a substantially sinusoidal outflow end, such as depicted in the figures. A sinusoidal outflow end, for example, has peaks at the respective commissures 26 and corresponding sinuses between adjacent peaks. Alternatively, the outflow end 16 could be configured to be generally circular by maintaining a length of valve wall substantially co-extensive with the axial length of the valve portion at the respective commissures 26. Similarly, the inflow end 14 can be generally sinusoidal having peaks and valleys corresponding to the outflow end peaks and valleys. Alternatively, the inflow end 14 can be a generally circular.

The prosthesis 12 also includes a generally annular support 30 disposed about the valve portion 12. The support 30 helps stabilize the prosthesis 10 both during and after implantation, such as by helping to maintain a desired cross-sectional dimension. The annular support 30 includes an inflow end 32 and an outflow end 34 spaced apart from the inflow end to define a sidewall portion thereof.

In the example embodiment shown in the figures, the outflow end 34 of the support 30 is dimensioned and configured according to the outflow end 16 of the valve portion 12. Thus, in the illustrated example, the outflow end 34 of the support 30 is generally sinusoidal having peaks 36 generally aligned with the commissures 26 of the valve portion 12. The axial length of the sidewall of the support 30 generally ranges from about ⅓ to about ⅔ of the axial length of the valve portion 12. The inflow end 32 of the support 30 can also be configured according to the contour of the inflow end 14 of the valve portion 12. Examples of some different types and configurations of supports that can be employed are shown and described in commonly owned U.S. Pat. No. 5,935,163, which is incorporated herein by reference.

The annular support 30 is positioned around the sidewall portion 18 intermediate the inflow and outflow ends 14 and 16, respectively, of the valve portion 12. The support 30 can be positioned coaxially around the valve portion 12, such as by sliding it over the sidewall portion 18 thereof. In a desired relative position, the inflow end 32 of the support 30 is spaced apart from the inflow end 14 of the valve portion 12 and the outflow end 34 of the support is spaced apart from the outflow end 16 of the valve portion. One or more sutures 38 can be applied to help secure the support 30 relative to the valve portion 12.

The support 30 can be formed of a substantially flexible material, such as a metal or plastic that is able to bend or flex without breaking. For instance, the flexible material should have a desired memory characteristic capable of returning to its original (e.g., generally circular cylindrical) shape after being deformed. The support 30, for example, can be formed of an elastic-type flexible material, such as Delrin. Those skilled in the art will appreciate various other materials that can be used to form the support 30.

The diameter of the support 30 generally depends on the size of the valve portion 12. In one embodiment, the support 30 has a radial thickness that is less than about 0.5 mm. Those skilled in the art will understand and appreciate that other radial thicknesses can be utilized depending on, for example, the desired stiffness of the prosthesis 10 and the type of material being used.

A sheath 40 of a substantially biocompatible material can be applied to cover the support 30 and at least a radially outer surface of the sidewall portion 18. In the particular example depicted in the figures, the sheath 40 covers the support 30 and the entire exposed sidewall portion 18. The sheath 40 can be secured relative to the sidewall portion 18 of the prosthesis 10 by one or more sutures 42. As an example, "mattress sutures" can be applied between the sheath 40 and the support 30 to maintain the axial positioning of the support intermediate the inflow and outflow ends 12 and 14 of the heart valve 10.

The sheath 40 could be any flexible biocompatible tissue material (natural or synthetic). In one embodiment, the sheath 40 is formed from one or more sheets of a biological tissue material, such as animal pericardium (e.g., bovine, equine, porcine, human, etc.), dura matter, collagen, peritoneum and the like. The biological tissue material may be chemically treated in a suitable fixation solution, such as including glutaraldehyde.

By way of further illustration, the sheath 40 may be formed from a NO-REACT® tissue product, which is commercially available from Shelhigh, Inc., of Millburn, N.J. as well as from distributors worldwide. The NO-REACT® tissue products help improve the biocompatibility of the apparatus 50, thereby mitigating the likelihood of a patient rejecting an implanted prosthesis that includes the apparatus. The NO-REACT® tissue also resists calcification when implanted. Those skilled in the art will appreciate various other materials that could be utilized for the sheath, including as cloth (e.g., Dacron) as well as other biocompatible materials (natural or synthetic).

In the illustrated example, the prosthesis 10 also includes an outflow extension 44 associated with each of a plurality of commissures 26 of the valve portion 10. The outflow extensions 44 extend a predetermined distance beyond as well as lateral to each the outflow end 16 of the valve portion at the respective commissures 26. The outflow extensions 44 can be formed of one or more sheets of any suitable flexible material, such as a natural tissue material (e.g., pericardium, dura matter or collagen) as well as a cloth or fabric material (e.g., Dacron). The outflow extensions 44 can be formed of the same or a different material from the sheath 40.

The support 30 can be configured to be sufficiently flexible, such that the support cannot of its own strength inhibit radial deflection of the commissures 26, such as during closure of the leaflets 20, 22 and 24 of the prosthesis when implanted. Accordingly, when implanting prosthesis 10, the outflow extensions 44 can conveniently be secured (e.g., by sutures) to the valve wall or other surrounding tissue of the patient. As a result, the aortic valve wall to which the outflow extensions are secured will inhibit the radial inward deflection of the commissures 26, thereby maintaining a desired shape of the prosthesis 10. As a result, improved coaptation between the leaflets 20, 22 and 24 can be provided.

In the particular example illustrated in the figures, the outflow extensions 44 are formed as an outflow extending portions of the sheath 40. That is, the outflow extensions 44 can be part of the sheath, which part extends a desired amount beyond the outflow end of the valve portion 12 aligned with the respective commissures 26. In the example in FIG. 1A, an outflow end 48 of the sheath 40 conforms and is substantially coextensive with the outflow end 16 of the valve portion 12, except that the outflow extensions 44 extend beyond the outflow end of the valve portion at the respective commissures 26. An inflow end portion 46 of the sheath 40 extends axially beyond an inflow end 14 of the valve portion 12. The inflow end portion 46 of the sheath 40 extends axially beyond the inflow end 14 of the valve portion, for example, a distance that approximates (or exceeds) a distance between inflow and outflow ends of the valve portion 12 at its sinuses.

Referring to FIGS. 2A and 2B, a strip 50 is disposed around the valve portion 12 intermediate the inflow end 14 and outflow end 16 thereof. A radially outer extent of the strip 50 extends radially outwardly beyond a radially outer sidewall surface of the support 30. In the example of FIGS. 2A and 2B, the strip 50 generally circumscribes the annular support 30. For instance, as depicted in FIG. 2B, the strip 50 has an axial dimension D2 that is less than an axial dimension D1 of the support 30. The strip 50 can also be positioned axially relative to the support 30 such that an inflow end 52 of the strip 50 is spaced apart from an inflow end 32 of the support 30. An outflow end 54 of the strip further can be spaced apart from the outflow end 34 of the support 30. That is, the strip 50 can positioned to be axially centered and to circumscribe a central portion of the support 30, such as shown in FIGS. 2A and 2B. Alternatively, the strip 50 can be oriented axially such that the inflow end 52 of the strip 50 is adjacent relative to an inflow end 32 of the support 30 or that the outflow end 54 is adjacent the outflow end 34 of the support.

The strip 50 can be formed of one or more layers of a pliant material, such as a biocompatible tissue material. For instance, the strip 50 can be formed of a biological tissue material, such as animal pericardium, dura matter, collagen, peritoneum or the like. Alternatively, the strip 50 can be formed of a natural or synthetic cloth-like material, such as Dacron or PTFE (polytetrafluoroethylene) or a plurality of sutures. The strip 50 can be in the form of a continuous annular strip. Alternatively, an elongate strip of a suitable material can be applied in a desired configuration around the valve portion and outer sheath 18 without connecting the ends thereof. Additionally or alternatively, the strip 50 can comprise more than one length of a suitable material.

Those skilled in the art will understand and appreciate that the radial thickness of the strip 50 can be increased by employing more than one strip or by selecting the material to have a desired thickness. The strip 50 thus can provide a pliant substrate for receiving sutures to secure the prosthesis at an annulus of a patient's heart valve.

Figure 3B:
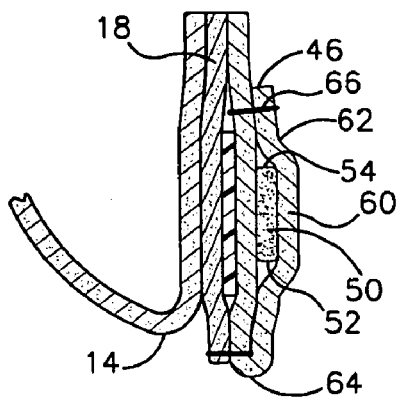
FIG. 3B is a partial cross-sectional view of the prosthesis of FIG. 2A

FIGS. 3A and 3B depict one example of a completed prosthesis 10 that according to an aspect of the present invention. The prosthesis 10 includes a biocompatible pliable covering 60 over the strip 50. In the example of FIGS. 3A and 3B, at least an inflow portion 64 of the covering 60 includes an outflow portion 62 that extends beyond an outflow end 54 of the strip 50. At least a portion of the covering 60 also extends axially beyond the inflow end 52 of the strip 50, such that the strip 50 is completely covered, as shown in FIGS. 3A and 3B. The covering 50 can be formed of any suitable biocompatible material, including, but not limited to, the materials described herein that can be utilized for the sheath 40. The covering 50 can be formed of the same or a different material from the sheath 40.

In the illustrated example of FIGS. 3A and 3B, the covering 60 can be formed by folding (or plicating) the inflow end portion 46 of the sheath 40 (see, e.g., FIGS. 2A and 2B) axially towards the outflow end 16 of the valve portion 12 to cover the strip 50, which defines a fold seam in the sheath at the inflow end of the prosthesis 10. The end portion 46 of the sheath 40, for example, can be folded such that its most inflow end is positioned adjacent or substantially coextensive the sinus regions of the valve portion 12, such as located axially between the outflow end 34 of the support 30 and the outflow end 16 of the valve portion 12. By folding the inflow extending portion 46 of the sheath 40 in this way, the prosthesis 10 can be provided with a lower profile inflow annulus when compared to many other prostheses.

What has been described above includes examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

Having described the invention, the following is claimed:

1. A heart valve prosthesis comprising:
   a valve member having an inflow end, an outflow end, and a generally cylindrical sidewall portion extending between the inflow end and the outflow end, the valve member including at least one leaflet moveable relative to the sidewall portion to provide for substantially unidirectional flow of fluid through the valve member;
   a support of a substantially flexible material positioned around the sidewall portion, wherein the support is positioned around the sidewall portion of the valve member intermediate the inflow end and the outflow end of the valve member, such that an inflow end of the support is spaced apart from the inflow end of the valve member and an outflow end of the support is spaced apart from the outflow end of the valve member;
   a strip of pliant material around valve member intermediate the inflow end and the outflow end of the valve member in a generally overlying relationship with the support;
   a covering over a radially outer exposed surface of at least the strip; and
   wherein the outflow end of the sidewall portion of the valve member includes alternating peaks and sinuses, the outflow end of the support includes alternating peaks and sinuses configured to follow the contour of the sinuses of the valve member.

2. The prosthesis of claim 1, wherein the strip comprises at leastone of a natural material and a synthetic material.

3. The prosthesis of claim 1, wherein the strip comprises a biological tissue material.

4. The prosthesis of claim 1, further comprising an outflow extension operatively associated with and extending axially beyond and lateral each of a plurality of commissures proximal an outflow end of the valve member.

5. The prosthesis of claim 1, wherein the valve member further comprises one of a homograft and a xenograft that includes at least two leaflets extending from a valve wall portion corresponding to the sidewall portion.

6. A heart valve prosthesis comprising:
   a valve member having an inflow end, an outflow end, and a generally cylindrical sideWall portion extending between the inflow end and the outflow end, the valve member including at least one leaflet moveable relative to the sidewall portion to provide for substantially unidirectional flow of fluid through the valve member;
   a support of a substantially flexible material positioned around the sidewall portion, wherein the support is positioned around the sidewall portion of the valve member intermediate the inflow end and the outflow end of the valve member, such that an inflow end of the support is spaced apart from the inflow end of the valve member and an outflow end of the support is spaced apart from the outflow end of the valve member;
   a strip of pliant material around valve member intermediate the inflow end and the outflow end of the valve member in a generally overlying relationship with the support;
   a covering over a radially outer exposed surface of at least the strip;

an outflow extension operatively associated with and extending axially beyond and lateral each of a plurality of commissures proximal an outflow end of the valve member; and a sheath of a flexible material that covers the support and at least a substantial portion of an exterior part of the sidewall of the valve member, the outflow extensions being formed as outflow extending portions of the sheath that extend a predetermined distance beyond each of the plurality of commissures proximal the outflow end of the valve member.

7. A heart valve prosthesis comprising:

a heart valve comprising:

a generally cylindrical sidewall portion extending between an inflow end and an outflow end; and at least one leaflet located within the sidewall portion, the at least one leaflet being moveable relative to the sidewall portion to provide for substantially unidirectional flow of blood through the heart valve;

a support apparatus around the sidewall portion and positioned axially between the inflow end and the outflow end of the sidewall portion, wherein an outflow end of the support is sinusoidal with peaks extending from a generally annular base portion corresponding to a contour of the outflow end of the sidewall portion of the heart valve, such that the peaks of the support are substantially aligned with corresponding commissures of the heart valve;

a strip of pliant material around the sidewall portion of the heart valve intermediate the inflow end and the outflow end of the sidewall portion and extending radially outwardly beyond a radially outer surface of the support;

a pliable covering over the strip and attached relative to the heart valve to inhibit axial movement of the strip relative to the heart valve; and a sheath of a flexible material interposed between the support and the strip, the sheath covering the support and at least a substantial part of the sidewall portion of the heart valve, the sheath having an inflow extending portion folded axially over a portion of the sheath that covers the support to define a fold seam adjacent the inflow end of the sidewall portion of the heart, a length of the sheath extending from the fold seam over the strip such that an end thereof terminates at a location adjacent an outflow end of the support.

8. The prosthesis of claim 7, further comprising an outflow extension operatively associated with and extending axially beyond and lateral each of a plurality of commissures of the heart valve proximal an outflow end of the sidewall portion of the heart. valve.

9. The prosthesis of claim 8, further comprising a sheath of a flexible material that covers the support and at least a substantial portion of an exterior part of the sidewall of the heart valve, the outflow extensions being formed as outflow extending portions of the sheath that extend a predetermined distance beyond each of the plurality of commissures of the heart valve proximal the outflow end of the sidewall portion of the heart valve.

10. The prosthesis of claim 7, wherein the support comprises a flexible material having a radial thickness of less than about 0.5 mm.

11. The prosthesis of claim 7, wherein the sheath is secured relative to the hears valve to inhibit axial movement of the strip relative to the heart valve.

12. The prosthesis of claim 7, wherein the sheath comprises a biological tissue material.

* * * * *

UNITED STATES PATENT AND TRADEMARK OFFICE
CERTIFICATE OF CORRECTION

PATENT NO. : 7,247,167 B2  Page 1 of 1
APPLICATION NO. : 10/782702
DATED : July 24, 2007
INVENTOR(S) : Shlomo Gabbay It is certified that error appears in the above-identified patent and that said Letters Patent is hereby corrected as shown below:

Claim 2 column 6, line 36, after "at" delete "leastone" and insert -- least one--.

Claim 6 column 6, line 49, after "cylindrical" delete "sideWall" insert --sidewall--

Claim 8 column 8, line 16, after "heart" delete "."

Claim 11 column 8, line 31, after "relative to the" delete "hears" insert --heart--

Signed and Sealed this

Twenty-fifth Day of September, 2007

JON W. DUDAS
*Director of the United States Patent and Trademark Office*